(12) United States Patent
Ingimundarson et al.

(10) Patent No.: US 7,513,880 B2
(45) Date of Patent: Apr. 7, 2009

(54) ANKLE-FOOT ORTHOSIS HAVING AN ORTHOTIC FOOTPLATE

(75) Inventors: Arni Thor Ingimundarson, Ladera Ranch, CA (US); Kim de Roy, Antwerp (BE)

(73) Assignee: Ossur HF, Reykjavik (IS)

( * ) Notice: Subject to any disclaimer, the term of this patent is extended or adjusted under 35 U.S.C. 154(b) by 208 days.

(21) Appl. No.: 11/651,513

(22) Filed: Jan. 10, 2007

(65) Prior Publication Data

US 2007/0197948 A1     Aug. 23, 2007

Related U.S. Application Data

(62) Division of application No. 10/927,135, filed on Aug. 27, 2004, now Pat. No. 7,270,644.

(60) Provisional application No. 60/500,227, filed on Sep. 5, 2003, provisional application No. 60/512,203, filed on Oct. 20, 2003, provisional application No. 60/576,294, filed on Jun. 3, 2004.

(51) Int. Cl.
*A61F 5/00* (2006.01)
(52) U.S. Cl. .......................... 602/23; 602/27
(58) Field of Classification Search .................. 602/23, 602/27, 60, 65; 128/882
See application file for complete search history.

(56) References Cited

U.S. PATENT DOCUMENTS

| | | | |
|---|---|---|---|
| 114,669 A | 5/1871 | Grant | |
| 433,227 A | 7/1890 | Beacock | |
| 735,860 A | 8/1903 | Darby | |
| 839,223 A | 12/1906 | Stevens | |
| 1,334,596 A | 3/1920 | Crouch | |
| 1,656,322 A | 1/1928 | Fischer | |
| 1,769,781 A | 7/1930 | Harrison | |
| 1,948,534 A | 2/1934 | Nelson et al. | |
| 2,492,920 A | 12/1949 | Koster | |
| 2,847,991 A | 8/1958 | Andrews | |
| 2,949,111 A * | 8/1960 | Ruotoistenmaki | 602/28 |
| 3,086,522 A | 4/1963 | Frohmader | |
| 3,171,407 A | 3/1965 | Rogers | |
| 3,304,937 A | 2/1967 | Callender, Jr. | |
| 3,345,654 A | 10/1967 | Noble | |
| 3,523,526 A | 8/1970 | Phelps | |
| 3,557,782 A | 1/1971 | Wafer | |
| 3,584,622 A | 6/1971 | Domenico | |
| 3,589,359 A | 6/1971 | Hill | |
| 3,606,884 A | 9/1971 | Peter | |

(Continued)

FOREIGN PATENT DOCUMENTS

DE          831872          2/1952

(Continued)

*Primary Examiner*—Michael A. Brown
(74) *Attorney, Agent, or Firm*—Bacon & Thomas, PLLC

(57) ABSTRACT

An ankle-foot orthosis including a footplate having a line of progression that extends from a heel portion to a middle portion to a toe portion of the footplate, and a leg support connected to the footplate. The footplate has at least two superimposed and discrete structural layers each having a different length and extending along at least a segment of a length of the footplate. The footplate defines regions with different thicknesses and stiffness. The leg support has a first end portion connected to the heel portion of the footplate.

7 Claims, 11 Drawing Sheets

U.S. PATENT DOCUMENTS

| | | |
|---|---|---|
| 3,618,946 A | 11/1971 | Lee |
| 3,779,654 A | 12/1973 | Horne |
| RE27,957 E | 4/1974 | Larson |
| 4,651,445 A | 3/1987 | Hannibal |
| 4,938,777 A * | 7/1990 | Mason et al. ................. 623/50 |
| RE33,762 E | 12/1991 | Lonardo |
| 5,219,324 A * | 6/1993 | Hall ............................ 602/28 |
| 5,226,875 A | 7/1993 | Johnson |
| 5,269,748 A | 12/1993 | Lonardo |
| 5,298,013 A | 3/1994 | Lonardo |
| 5,372,576 A | 12/1994 | Hicks |
| 5,431,624 A | 7/1995 | Saxton et al. |
| 5,569,173 A | 10/1996 | Varn |
| 5,569,174 A | 10/1996 | Varn |
| 5,716,336 A | 2/1998 | Hines et al. |
| 5,799,659 A | 9/1998 | Stano |
| 5,817,041 A | 10/1998 | Bader |
| 5,897,515 A | 4/1999 | Willner et al. |
| 6,146,344 A | 11/2000 | Bader |
| 6,560,902 B1 | 5/2003 | Eschweiler |
| 6,676,618 B2 | 1/2004 | Andersen |
| 6,945,947 B2 | 9/2005 | Ingimundarson et al. |
| 7,112,180 B2 | 9/2006 | Gunther |
| 7,270,644 B2 * | 9/2007 | Ingimundarson ............. 602/27 |

FOREIGN PATENT DOCUMENTS

| | | |
|---|---|---|
| DE | 2A237171 | 4/1954 |
| DE | 4214831 A1 | 11/1993 |
| DE | 93 19 050.6 | 3/1994 |
| DE | 197 22 118 A1 | 2/1999 |
| DE | 299 09 981 U1 | 1/2000 |
| DE | 199 05 544 A1 | 8/2000 |
| EP | EO 0 931 525 | 7/1999 |
| GB | 2188550 A * | 10/1987 |
| WO | WO 92/05751 | 4/1992 |
| WO | WO 97/28762 | 8/1997 |
| WO | 03/002042 A1 | 1/2003 |

* cited by examiner

|  | 44-59 kg | 60-77 kg | 78-100 kg | 101-116 kg |
|---|---|---|---|---|
| max. rigidity | Category II | Category III | Category IV | Category IV |
| med. rigidity | Category I | Category II | Category III | Category IV |
| min. rigidity | Category I | Category II | Category II | Category III |
FIG. 17
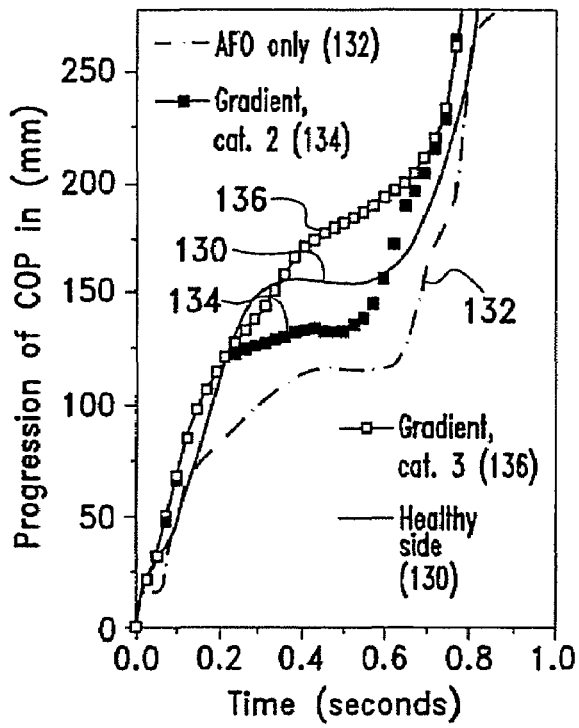
FIG. 18
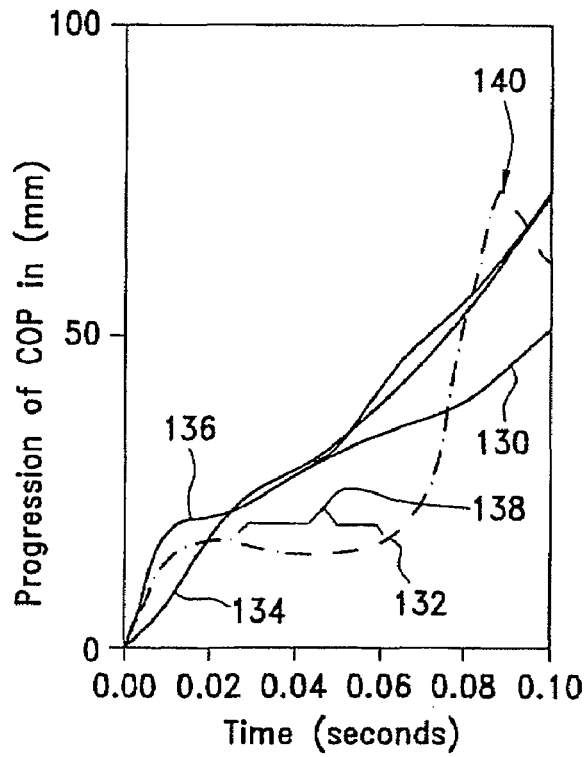
FIG. 19

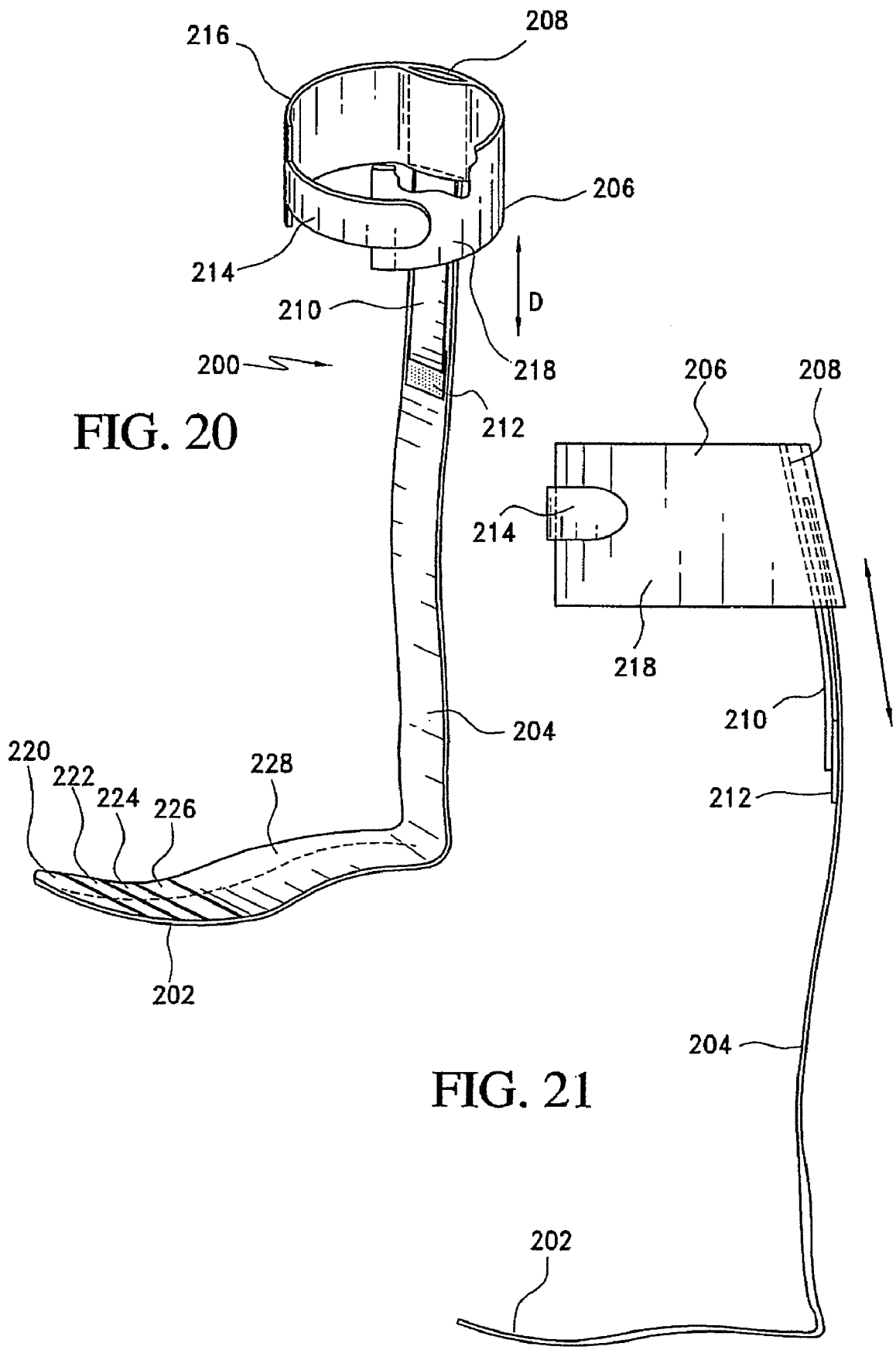

|  | Small | Medium | Large |
|---|---|---|---|
| Foot size | 10"(250mm) | 10 3/4" (270mm) | 11 1/2"(290mm) |
| Footplate | 9 3/4(240mm) | 10 1/4" (260mm) | 11"(280mm) |
| Height thickest part of the calf | 12 1/2"-14 1/4" (320-360mm) | 13 1/4"-15" (340-380mm) | 14 1/4"-15 3/4" (360-400mm) |
| Proximal strap height (standard) | 13 1/4"(340mm) | 14 1/4" (360mm) | 15"(380mm) |

ANKLE-FOOT ORTHOSIS HAVING AN ORTHOTIC FOOTPLATE

This application is a divisional application of U.S. application Ser. No. 10/927,135 which claims the benefit of U.S. Provisional Application Nos. 60/500,227 filed Sep. 5, 2003, 60/512,203 filed Oct. 20, 2003, and 60/576,294 filed Jun. 3, 2004.

BACKGROUND

Foot orthotics are often used to compensate for impaired foot function by controlling abnormal motion across the joints of the foot. Specific impairments that a foot orthotic may assist include mild "foot drop" due to neurological conditions, orthopedic gait abnormality, clubfoot, mid-tarsal fracture, partial foot amputation, arthritis, hallux valgus, hallux rigidus, turf toe, and plantar fasciitis. Foot orthotics may also be prescribed to reduce pain, to provide support, to prevent foot deformity or prevent the worsening thereof, to relieve pressure on a certain area of the foot, and to improve the overall biomechanical function of the foot and lower extremity limbs.

In their basic form, functional foot orthotics or orthotic footplates work like shock absorbers, removing pressure and stress from painful areas of the foot and ankle while controlling abnormal position and movement of the foot. Moreover, they promote the proper alignment of the feet and can restore balance. Orthotic footplates operate to hold the heel and middle portion of a foot in a more stable position when a person is walking or standing, and thus allow the foot to function more efficiently during weight-bearing and propulsion.

Known orthotic footplates tend to have an equal stiffness along their length. It has been found, however, that a footplate having equal stiffness may further contribute to an abnormal gait by overcompensating a foot at a toe portion. More specifically, during toe-off of a gait cycle, the toe portion has a tendency to bend around the largest moment of the footplate. This, in turn, results in a considerable amount of pressure being placed on the plantar surface of the foot. Hence, these orthotic footplates may actually worsens a condition and create orthopedic problems elsewhere in the body.

Accordingly, it is desirable to provide an orthotic footplate that has a stiffness gradient that corresponds to ground reaction forces as they are applied to a foot and released by a foot during a swing phase of a gait cycle, while providing the necessary support and shock absorption to a foot during a stance phase of a gait cycle.

In addition to foot impairment, an ankle-foot orthosis is often prescribed for users having gait deviations that relate to muscle weakness. An ankle-foot orthosis substitutes or compensates for weak dorsiflexors during the swing phase and for weak plantarflexors during the stance phase of a user's gait. In effect, an ankle-foot orthosis can be used to support and align the ankle and the foot, suppress spastic and overpowering ankle and foot muscles, to assist weak and paralyzed muscles of the ankle and foot, to prevent and correct ankle and foot deformities, and to improve the functions of the foot.

Many known ankle-foot orthoses are configured to concentrate on the ankle and knee biomechanics while only providing minimal support to the foot. It has been found, however, that users of ankle-foot orthoses require at least some foot support of the type offered by the aforementioned orthotic footplates.

Accordingly, it is desirable to provide an ankle-foot orthosis having an orthotic footplate that improves biomechanical function of the foot, ankle and knee. Furthermore, it is desirable to provide an ankle-foot orthosis imparting improved stability of a foot and leg over conventional ankle-foot orthoses while maintaining a lightweight structure that comfortably secures to a user's foot while providing suitable support.

SUMMARY

According to an embodiment of the present invention, an orthotic footplate is provided having variable elasticity and adapted to provide a support for a user foot. The footplate generally defines a line of progression that extends form a heel portion to a middle portion to a toe portion. The footplate comprises a layered structure of two or more discrete structural layers. Each layer extends along at least a segment of a length of the footplate wherein different regions are defined having different thicknesses and stiffness. In this embodiment, the difference in thickness of the footplate is defined as being substantially perpendicular to a line of progression extending from a heel portion to a middle portion to a toe portion of the footplate.

Corresponding to a feature of an embodiment of the footplate, the first structural layer is coextensive with the length of the footplate, whereby the first layer generally defines the periphery of the footplate. Additional structural layers are superimposed on a surface of the first structural layer of the footplate wherein ascending structural layers generally decrease in length relative to the first layer.

The additional structural layers each have an edge thickness that extends substantially perpendicular from an adjacent lower structural layer. In variations of this embodiment, edge thickness differences may also have a convex or a concave shape. By arranging an edge thickness that is substantially perpendicular to the line of progression enable easier control of the flexibility of the footplate as opposed to when the edge thickness is concave or convex. The distance between borders where the thickness between two or more layers is different determines at least partly the flexibility of the footplate in a way that the flexibility is more continuous when the distance is short or discontinues when the distance is increased.

According to a variation of the embodiment, the first structural layer or the additional structural layers are woven with fibers running substantially 45° and −45° to the line of progression. The layer or layers may be arranged unidirectionally with fibers running substantially parallel to the line of progression.

The stiffness and elasticity of the footplate may be tuned by varying the number of the layers, by varying the thickness of the layers, varying the material of the layers, or a combination thereof.

The distance between the borders where the thickness between two or more layers is different determines at least partly the flexibility of the footplate in a way that the flexibility becomes more continuous when the distance is short or discontinues when the distance is increased.

According to a variation of the footplate, the footplate may comprise additional areas of different thicknesses and thereby elasticity adapted to guide the gait pattern of an impaired foot to a normal gait pattern.

In another variation of the footplate, the footplate comprises a leg support fastened to the footplate, wherein the size and shape of the leg support may be varied depending on the application and the gait pathology of a user.

The embodiments of the orthotic footplate provide enhanced gait efficiency and comfort for those with partial foot amputation or other injuries requiring immobilization. Furthermore, the embodiments of the orthotic footplate offer a durable and dynamic footplate that imparts good support. When selected for the correct weight and activity category, the footplate redistributes effectively the forces directed onto the foot, allowing the most natural gait possible. As a result of its configuration, the orthotic footplate may be either customized or prefabricated to satisfy a variety of criteria and foot sizes.

According to another embodiment of present invention, an ankle-foot orthosis device having a footplate with variable elasticity is provided. The ankle-foot orthosis includes an embodiment of the footplate that has a line of progression extending from a heel portion to a middle portion to a toe portion. The footplate includes at least two superimposed, discrete structural layers each having different lengths and extending along at least a segment of a length of the footplate such that the footplate defines regions with different thicknesses and stiffness. The ankle-foot orthosis also includes a leg support that is connected to the heel portion of the footplate.

Corresponding to this embodiment of the ankle-foot orthosis, the ankle-foot orthosis includes a securing device that is arranged to secure the leg support to a user's leg. The securing device includes a slot that is configured to accommodate an end portion of the leg support, and a fastening device that has elastic properties and connects to the leg support to permit the securing device to move relative to the leg support.

In another variation of the ankle-foot orthosis, the leg support includes a spring member that connects to the heel portion of the footplate, and a leg shell having outwardly extending side portions adapted for supporting a user's leg. The footplate also includes outwardly extending side portions extending from the middle portion and around the heel portion of the footplate.

According to yet another embodiment of the ankle-foot orthosis, the leg support comprises first and second spring members that are each connected at one end to a heel portion of a foot support. A connecting element is provided which secures the first and second spring members together. The first spring member is connected at another end to a calf support member having two outwardly extending side portions adapted for securing to a user's leg.

The embodiments of the ankle-foot orthosis impart the benefits of the embodiments of the orthotic footplate described herein while resolving various problems related to biomechanics. The ankle-foot orthoses described herein can provide support, protection or replacement of lost function to users having foot, ankle and leg impairment.

BRIEF DESCRIPTION OF THE DRAWINGS

These and other features, aspects, and advantages of the present invention will become better understood with regard to the following description, appended claims, and accompanying drawings where:

FIG. 17 is a selection chart used in the selection of orthotic footplates;

FIGS. 18 and 19 are graphical representations showing a plot having a progression of center of pressure as a function of time;

FIG. 20 is perspective view of an embodiment of an ankle-foot orthosis according to the invention;

FIG. 21 is an elevational view of the ankle-foot orthosis of FIG. 20;

DETAILED DESCRIPTION OF VARIOUS EMBODIMENTS

A. Overview

Figure 1:
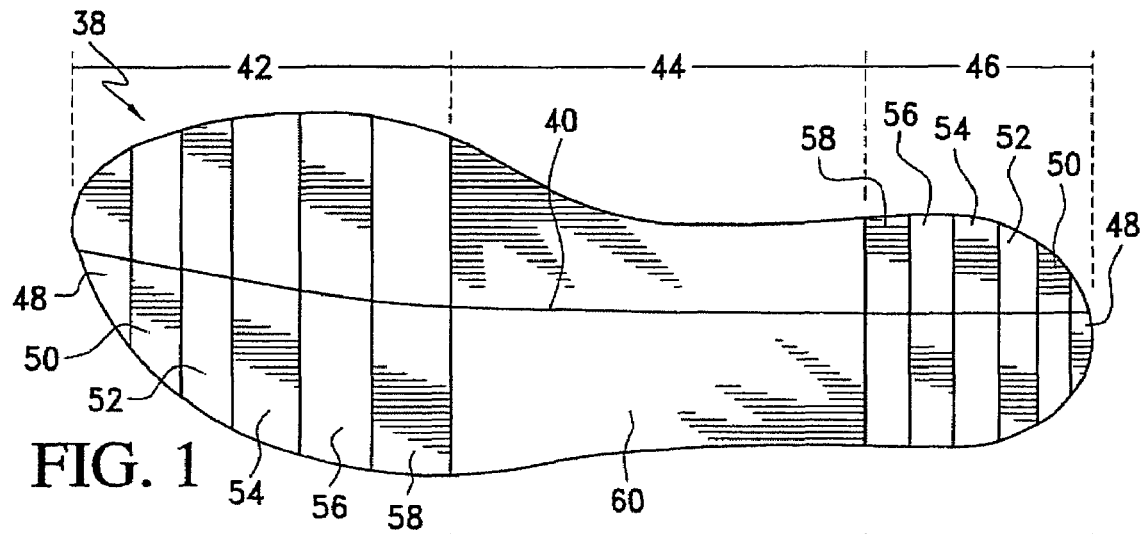
FIG. 1 shows a top plan view of an embodiment of an orthotic footplate.

A better understanding of different embodiments of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. § 112, paragraph 6.

B. Environment and Orientation of Footplate

In each of the embodiments described herein, the orthotic footplate defines a line of progression extending from a heel portion to a middle portion to a toe portion of the footplate. The line of progression basically defines a position curve of center of mass along the foot during a stance phase. While various embodiments described herein have different properties and structural configurations, each footplate generally possesses the above-mentioned portions. Moreover, the footplate may be divided into more portions, however, for simplicity and the sake of explanation, the following disclosure will remain limited to the abovementioned portions.

In accordance with the orthotic footplate, it will be understood that greater stiffness of the footplate is achieved at least by increasing the amount of layers or the thickness thereof at certain portions of the footplate. Conversely, greater elasticity is obtained at least in part in portions of the footplate having fewer or thinner layers.

The orthotic footplate may be modified to include a variety of different layers and define different thicknesses, lengths and shapes. It is to be understood that it is envisioned that as with users having different foot sizes and shapes, the orthotic footplate may likewise be modified to define such corresponding sizes and shapes.

Reference will be made herein to the gait cycle of a human being. The gait cycle is broken down into two components: the swing phase and the stance phase.

The swing phase last from the point when the toe leaves the ground until the moment when the heel comes into contact with the ground. At toe-off the foot is in a supinated position, and to assist in clearing the toe from the ground, it originally pronates. The remainder of the swing phase, the foot supinates prior to bringing the heel to the ground for the stance phase of the gait cycle.

The stance phase may be broken down into three portions: contact, midstance and propulsion. During the contact portion, the foot acts to absorb the shock of each step. The foot pronates to become more flexible in order to prevent transmission of the full force of each step to more proximal structures. During the midstance portion, the foot begins to supinate, transforming from a flexible shock absorber to a rigid level for propulsion. This period ends when the heel lifts off the ground, and the propulsive period begins. In the propulsion phase, the foot continues to supinate, propelling the body forward and ends with toe-off.

C. Description

Figure 2:
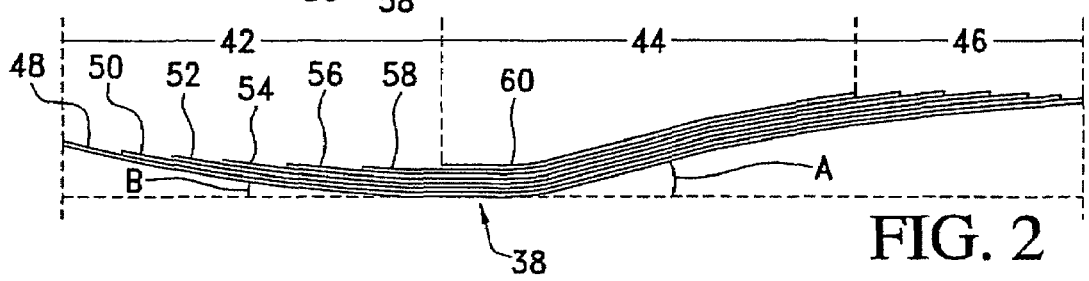
FIG. 2 shows an elevational view of the orthotic footplate of FIG. 1.
Figure 3:
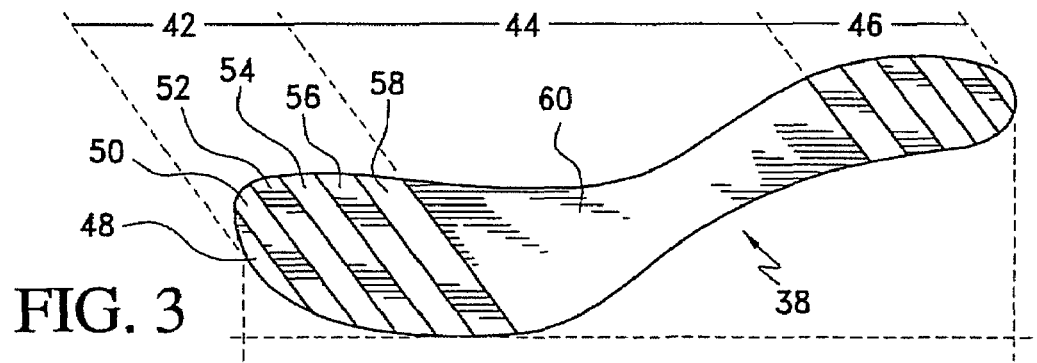
FIG. 3 shows a schematic view of several layers of the orthotic footplate of FIG. 1.

FIGS. 1-3 show an embodiment of an orthotic footplate 38 that is adapted to respond to ground reaction forces applied during various activities, such as compensation for loss of biomechanic foot-function. The footplate 38 defines line of progression 40, toe portion 42, middle portion 44, and heel portion 46. In this embodiment, the footplate 38 has a constant elasticity in the middle portion 44, but varies stiffness at the toe and heel portions 42, 46.

In this embodiment, the peripheral shape of the footplate 38 is defined by a first discrete structural layer 48 that essentially defines a distal or bottom portion of the footplate 38, and is generally arranged for facing towards a walking surface. The first layer 48 generally corresponds to the shape of a user's foot (not shown). Additional discrete structural layers 50, 52, 54, 56, 58, 60 are generally superimposed on the first layer 48 and extend proximally therefrom. Each layer rising from the first layer 48 is generally shorter in length than the first layer 48, wherein the length of the additional layers are reduced in both the toe and heel portions 42, 46.

Figure 4:
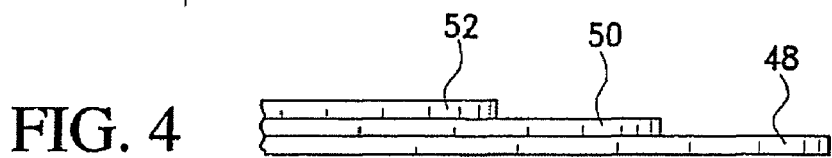
FIG. 4 is a perspective view of the orthotic footplate of FIG. 1.

FIG. 4 schematically shows the difference in length of the additional layers 50, 52 extending proximally from the first layer 48. While the thickness of each of the layers 48, 50, 52 is generally shown as the same, the thicknesses of each of the layers may be individually increased or decreased in order to obtain desirable properties such as stiffness.

Since the thickness difference of the layers is used to change the elasticity of the footplate, and thereby the stiffness, the edges of each of the additional layers at the toe and heel portions 42, 46 are generally linear and perpendicular to the line of progression 40. It has been found that when the edges are not perpendicular to the line of progression, it is difficult to control the elasticity of the footplate since non-uniform edges, such as those that are concave or convex shaped, have a tendency to generate a stiffness gradient across the length thereof. It will be understood, however, that the embodiments described herein may have layers with edges oriented relative to the liner of progression that are concave, convex, stepwise, linear, serrated, and combinations thereof if a stiffness gradient across the width of the footplate is desired. It will be noted, however, that attention must be made to ensure that the stiffness gradient does not adversely affect the function of the footplate The structural material of the layers preferably comprises carbon fibers impregnated with a thermoplastic material, such as polypropylene or nylon, or a resin. Alternatively, other structural materials may be used alone or in combination with carbon fibers. Such other structural materials include Kevlar aramid fibers, glass fibers or combinations thereof. The fibers are preferably impregnated with an epoxy resin or other suitable resin system. Alternatively, the footplate may be molded or comprise a plurality of polymeric layers, such as polypropylene, polyurethane or polyethylene. In each of the embodiments, the layers are bonded by using methods known to those skilled in the art.

According to one embodiment, the carbon fibers of the first layer are woven in an orientation substantially 45° and −45° to the line of progression. An advantage of having the fibers running substantially 45° and −45° to the line of progression is to prevent subsequent layers from untwisting. Alternatively, the fibers may be arranged in different orientations relative to the line of progression. The additional layers may be arranged similarly as the fibers in the first layer or in other orientations.

At least some of the additional layers may be unidirectional fibers that are oriented in generally single direction running substantially parallel to the line of progression. The orientation of these fibers is provided to maintain a large stiffness in a walking direction and to thereby minimize the thickness of the layer.

The footplate may be canted along different portions along the line of progression. As exemplified in FIG. 2, angle A is defined between the middle portion 44 and heel portion 46, wherein the transition of angle A occurs generally within the middle portion 44. Also, angle B exists between the toe portion 42 and the middle portion 44. By varying the height of the heel portion 46 and the height of the toe portion 42, one may facilitate roll over of a foot. A variety of angles for angles A, B are envisioned, with preferred angles ranging between 0-30°. Of course, other angles are possible and may be selected to accommodate a shoe type and a user's needs. Moreover, each of the portions of the footplate may comprise additional areas that are canted or have extended or shortened areas of transition.

With the exemplary footplate 38 shown in FIGS. 1-3, a footplate is provided having different areas of stiffness and flexibility so as to redistribute forces applied to the foot. The footplate increases the stability of the foot, releases energy and propels a user's foot and leg at toe-off. Moreover, the footplate raises a user's toes for clearance during the swing phase. The configuration of the footplate results in energy storage and energy release as it undergoes flexion and deflexion during a user's gait.

Figure 5:
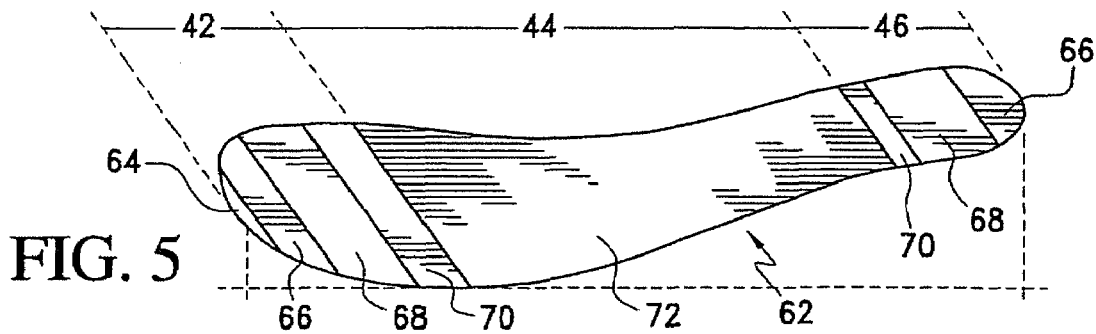
FIG. 5 is a perspective view of a variation of the orthotic footplate of FIG. 1.

According to different embodiments of the footplate, the length of the additional layers may be varied according to a desired stiffness in designated areas. The footplate 62 in FIG. 5 is exemplary in illustrating a first layer 64 and additional layers 66, 68, 70, 72 having different lengths across the toe, middle and heel portions 42, 44, 46. The second layer 66 generally extends into both the toe and heel portions 42, 46 of the footplate 62 in different proportions. In this embodiment, the second layer 66 extends into the heel portion 46 coextensively with the first layer 64, yet extends into the toe portion 42 less than the first layer 64. The configuration of the second layer 66 in this embodiment results in a stiffer heel portion 46 compared to the toe portion 42. The third layer 68 extends more into the heel portion 46 than in the toe portion 42 of the footplate 62, once again contributing to a stiffer heel portion 46. The fourth layer 70 extends more into the toe portion 42 than in heel portion 46 thus providing greater stiffness at the toe portion 42. Lastly, the fifth layer 72 defines a more elongate middle portion 44 of the footplate 62.

Figure 6:
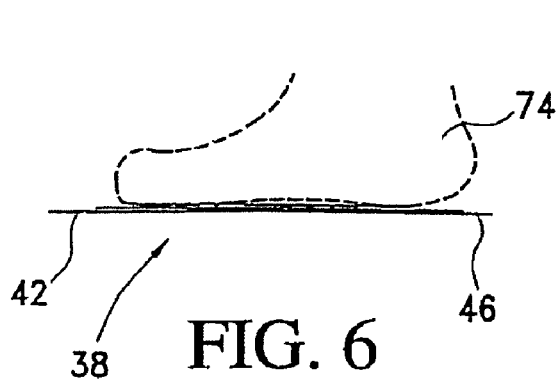
FIGS. 6-11 are schematic views showing dynamic energy storage and energy return of the orthotic footplate of FIG. 1.
Figure 9:
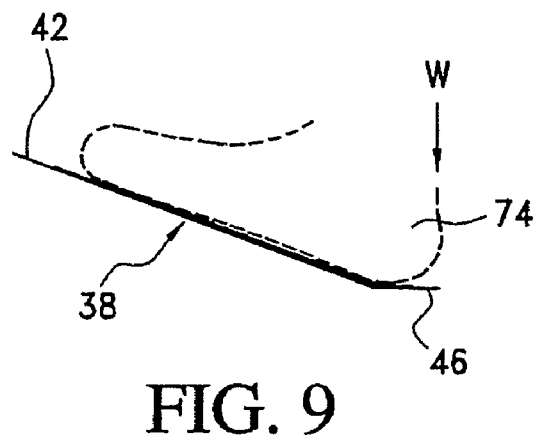
Figure 7:
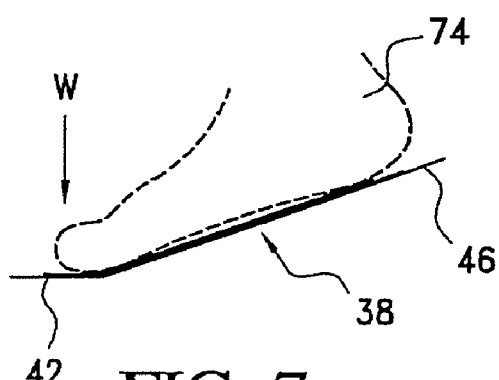
Figure 10:
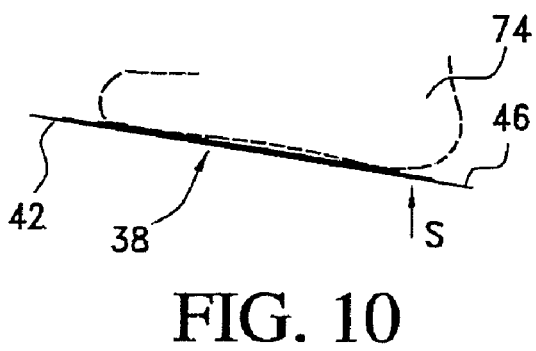
Figure 8:
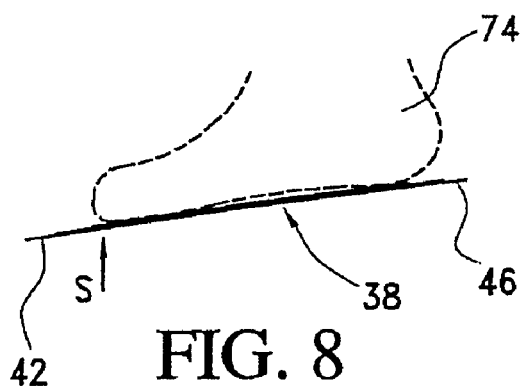
Figure 11:
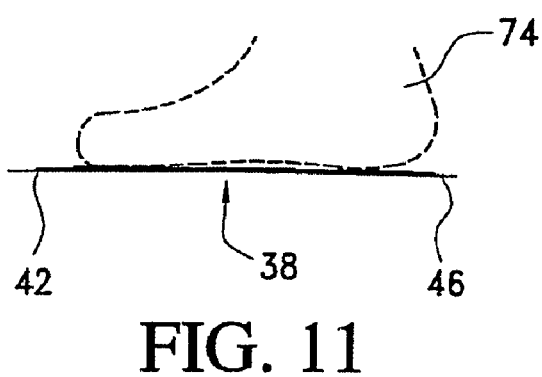

FIGS. 6-11 exemplify the energy storage and return of the footplate 38 in the embodiment of FIG. 1. FIG. 6 shows an impaired foot 74 of a user on the footplate 38 in a neutral position. In FIG. 7, the weight W of the user is exerted onto the toe portion 42 of the footplate which urges the footplate 38 to bend at the toe portion 42 and stores energy in the footplate 38. FIG. 8 shows the release of the weight W whereby energy S is released and propels the foot 74 at toe-off. In FIG. 9 the weight W of the user is used to bend the footplate 38 at the heel portion 46 and causes energy to be stored in the footplate 38. FIG. 10 shows the release of the weight W and the spring of the energy S to release. FIG. 11 shows the foot 74 pressing onto the footplate 38 in a neutral position similar to FIG. 6.

Figure 12:
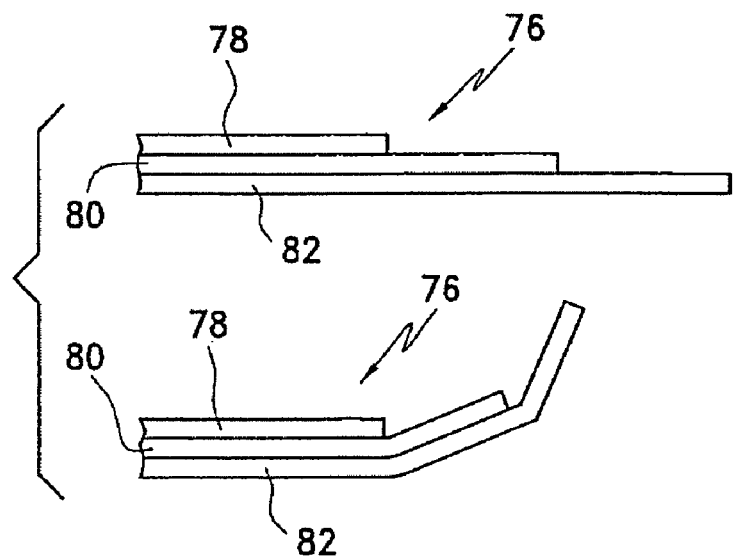
FIGS. 12 and 13 are schematic elevational views showing flexure of a heel portion of embodiments of an orthotic footplate.
Figure 13:
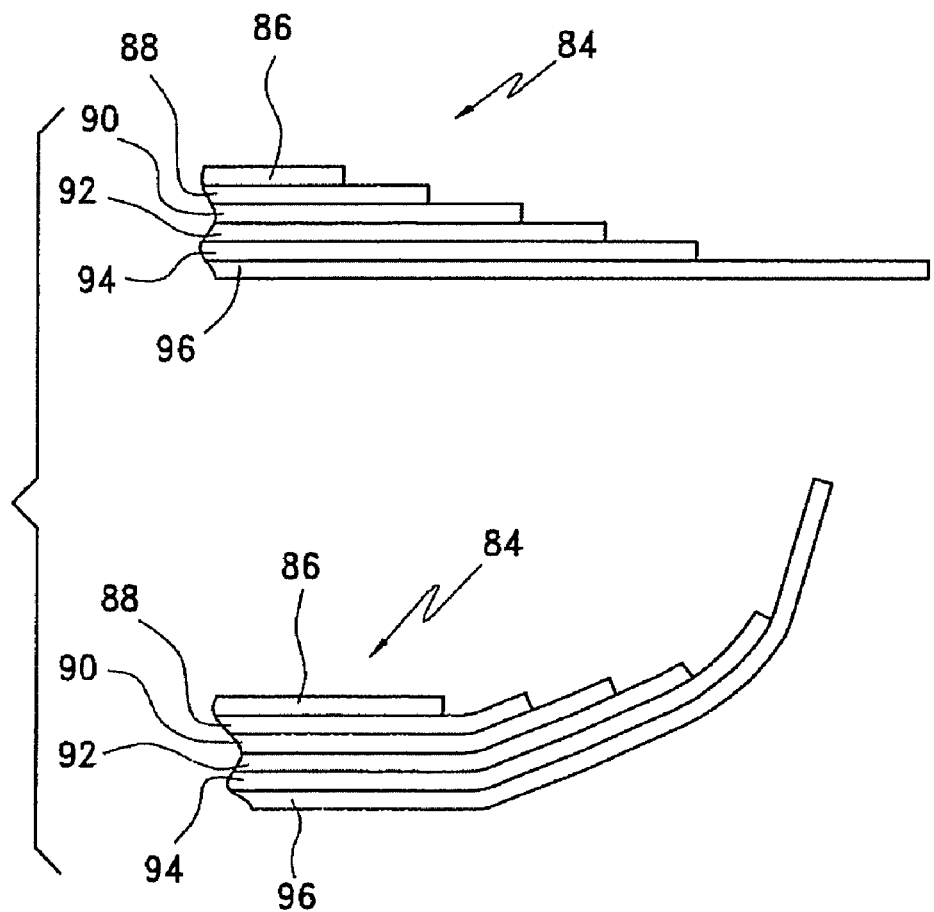

FIGS. 12 and 13 show heel portions of first and second different footplates 76, 84, and demonstrate how varying the amount of structural layers affect the flexure of the footplate. For exemplary purposes, each of the first and second footplates 76, 84 generally has the same overall thickness. The first footplate 76 includes three structural layers 78, 80, 82 that define a total thickness that is generally the same as a total thickness of six structural layers 86, 88, 90, 92, 94, 96 of the second footplate 84. The three structural layers 78, 80, 82 each have a greater thickness than each of the six structural layers 86, 88, 90, 92, 94, 96.

As can be seen in the depiction in FIGS. 12 and 13 of the flexed footplates 76, 84, the flexure of the first footplate 76 is less continuous and smooth than the flexure of the second footplate 84. Thus, embodiments of the footplate may be varied according to a desired smoothness of flexure of the footplate. It will also be pointed out that while the structural layers are shown as generally having the same thickness, the footplate is not limited to structural layers having a uniform thickness and may be modified to include a variety of structural layers having different thicknesses.

Figure 14:
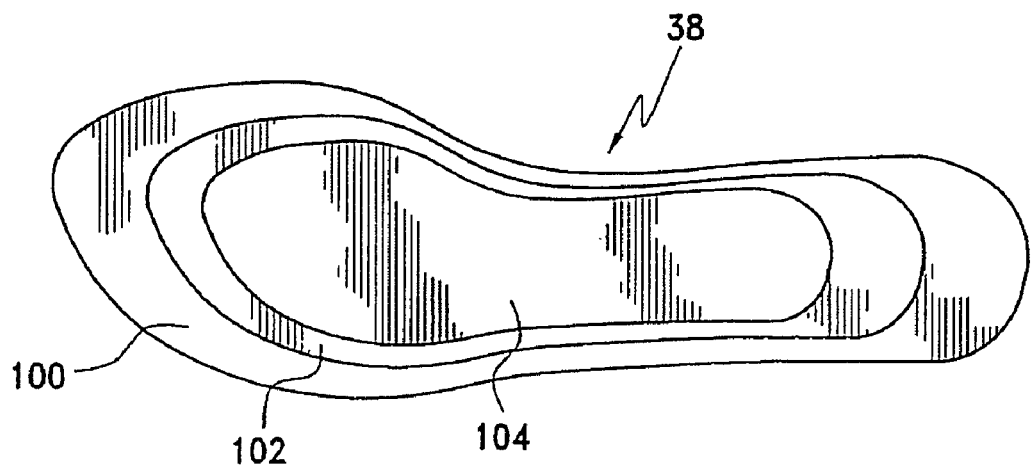
FIG. 14 is a schematic top plan view of another embodiment of an orthotic footplate.
Figure 15:
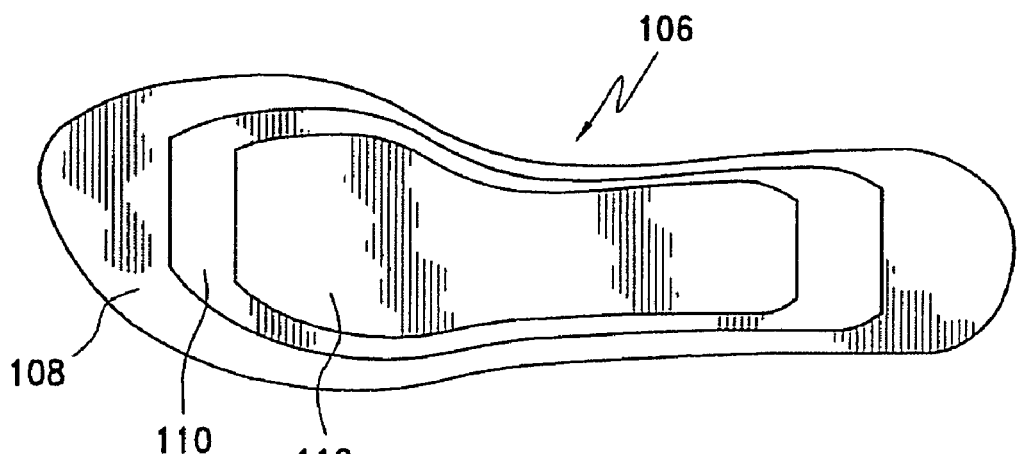
FIG. 15 is a schematic top plan view of another embodiment of an orthotic footplate.

FIGS. 14 and 15 illustrate first and second embodiments of orthotic footplates 98, 106 having structural layers of different shapes and sizes. As shown in FIG. 14, the first embodiment 98 includes three superimposed layers 100, 102, 104 that generally have the same but are of different proportions relative to one another. Alternatively, FIG. 15 shows the second embodiment 106 including three superimposed layers 108, 110, 112 wherein the first layer 108 generally defines the shape of a foot, and second and third layers 110, 112 generally follow the contoured shape of the first layer 108 except at the ends of the toe and heel portions which are substantially defined as linear edges.

It will be pointed out that it is within the scope of this invention to provide a variety of different superimposed structural layers having different shapes, areas, lengths, thicknesses, and other properties aimed at providing tailoring of the orthotic footplate to address the needs of a user.

Figure 16:
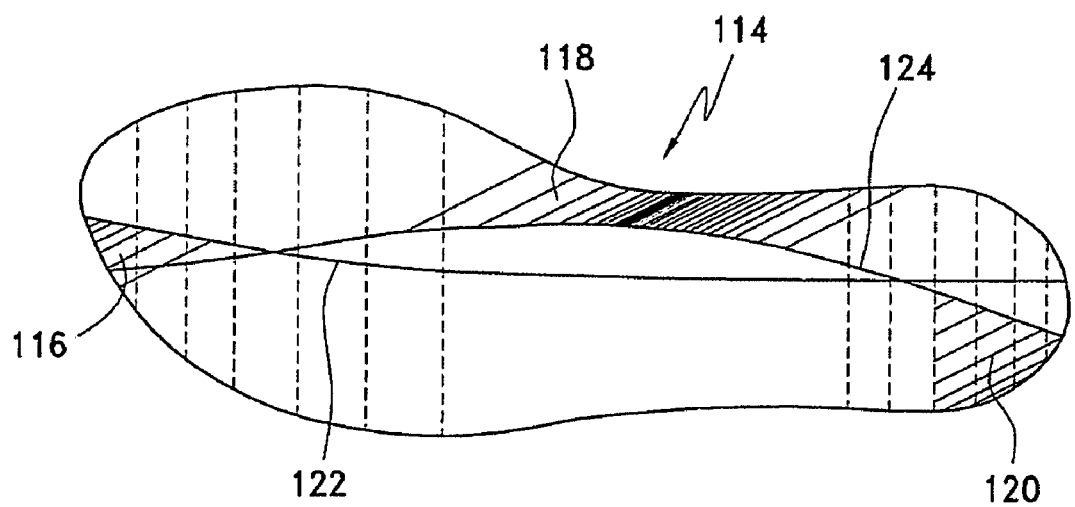
FIG. 16 is a schematic top plan view of another embodiment of an orthotic footplate.

FIG. 16 shows another embodiment of an orthotic footplate 114 similar to the embodiment of FIG. 10 yet differing therefrom by including the additional feature of having areas 116, 118, 120 of different thickness. The footplate 114 defines two lines of progression 122, 124 wherein the first line 122 defines a normal line of progression for a healthy foot and the second line 124 defines the line of progression for a particular impaired foot. The areas of differing thickness 116, 118, 120 are provided to accommodate a particular impaired foot by guiding the gait pattern to follow the normal line of progression 122.

The areas defining different thicknesses may be formed by additional segments of structural material or layers, and the structural layers themselves may have a non-uniform thickness which when superimposed with one another yields such areas of differing thickness.

FIG. 17 represents a selection chart of different footplates, which are divided into four weight categories and three rigidity categories including minimum, medium and maximum rigidity.

A footplate having maximum rigidity may be prescribed for users that have at least some of the following characteristics:

lack of a full-length toe-lever due to amputation of (parts of) the foot;

lack of a full-length toe-lever due to congenital deformities of the foot (for example, clubfoot);

severe and painful limitations of the distal joints of the foot that do not tolerate a normal amount of dorsiflexion at the metatarsal break;

severe cases of Hallux Valgus where no dorsiflexion tolerated.

A footplate having medium rigidity is recommended for users that have at least some of the following characteristics:

lack of part of the full-length toe-lever due to amputation of one or more of the toes;

considerable limitations of the meta-tarsophalangeal and interphalangeal joints of the toes due to any form of degenerative diseases that do not tolerate a normal amount of dorsiflexion of the metatarsal break;

severe hallux limitus to halux rigidus;

considerable Hallux Valgus.

A footplate having minimum rigidity may be prescribed for users that have at least some of the following characteristics:

light-weight users that lack part of the full-length toe-lever due to amputation of one or more of the toes;

mild limitation of the meta-tarsophalangeal and interphalangeal joints of the toes due to any form of degenerative diseases, that do not tolerate a normal amount of dorsiflexion at the metatarsal break;

mild hallux limitus to halux rigidus;

early stage hallux valgus.

FIGS. 18 and 19 graphically illustrate the progression of center of pressure "COP" (mm) as a function of time for a stance phase of a user's gait. At the beginning of the stance phase, the COP lies on the medial-posterior heel. The COP then moves through the mid-foot region and continues towards the forefoot, crossing the metatarsal heads to terminate in the region of the largest and the second toe. Significant distorsions of this pattern can give evidence of abnormal loads on the foot and of problems in the correct progression of a gait stride.

The graphical representation in FIG. 18 is based on measurements of a user wearing a plastic ankle-foot orthosis. Curve 130 marked as "healthy side" is used as a reference curve and represents a healthy foot. Curve 132 marked as "ankle-foot orthosis only" represents a user wearing only an ankle-foot orthosis without a footplate according to this disclosure. Curves 134 and 136, marked as "Gradient, cat. 2" and Gradient, cat. 3," respectively, define conditions of a user is wearing one of two different categories of orthotic footplates according to this disclosure that have different elasticity in combination with a plastic ankle-foot orthosis.

FIG. 19 is an exploded view of a portion of the plot shown in FIG. 18. The plateau 138 for curve 132 representing the ankle-foot orthosis indicates a poor gait pattern, whereas curves 134, 136 have a path substantially similar to the curve 130 of a healthy foot which is aligned in a proper orientation due to the footplate.

Evaluation of the graph shows the following results: at initial contact, the user shows an irregular progression of the center of pressure when only wearing the ankle-foot orthosis. The progression is shown as being slow and not smooth which is represented by peak 140. For both of the footplates used, at initial contact the progression is shown as being smoother and closely approximating the curve 130 of a healthy foot.

Looking at the midstance of curve 132, very little and slow progression of the COP is shown. Combining the ankle-foot orthosis with a footplate of category 2, the progression is smoother and faster. By the same token, when combining the ankle-foot orthosis with a footplate of category 3 a fluent progression of the center of pressure is measured.

Figure 22:
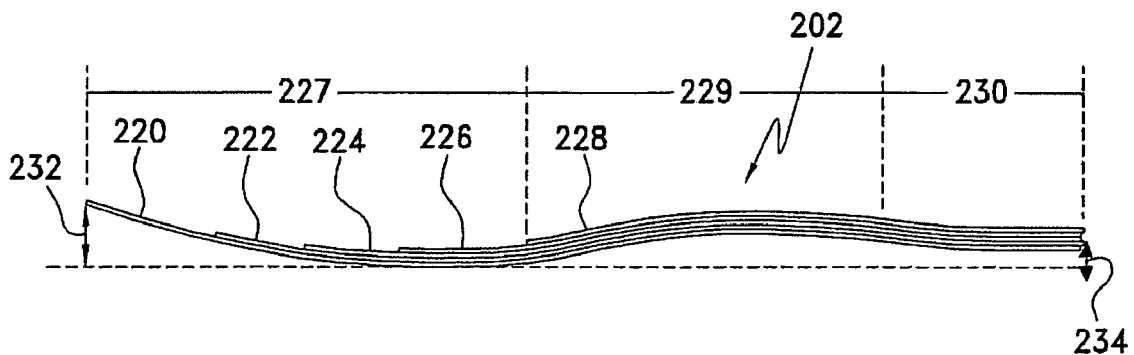
FIG. 22 is an elevational view showing the footplate of FIG. 20.

Turning to ankle-foot orthosis embodiments of the invention employing embodiments of the above-mentioned orthotic footplate, FIGS. 21 and 22 illustrate an embodiment of an ankle-foot orthosis adapted to assist the biomechanics of the foot, ankle and lower leg. In this embodiment, the ankle-foot orthosis 200 comprises a footplate 202 and a leg support 204 substantially formed as a single unit. The shape of the leg support 204 is generally defined as having a custom shape of a calf of a user, or may be based on a common calf shape. The length of the leg support 204 may easily be varied depending on the application and the user.

In the ankle-foot orthosis 200, thickness differences between adjacent layers are only shown in the footplate 202, which was generally discussed above in reference to the embodiment shown in FIG. 1

The ankle-foot orthosis 200 further includes a securing device 206 for extending circumferentially around a user's leg (not shown). The securing device 206 includes two end portions 216, 218 having a generally curvilinear profile, and a connecting element 214 connecting the end portions 216, 218. The securing device 206 is arranged to slide on the leg support 204 through a slot 208 which acts as a sliding means for the leg support 204. According to this embodiment, the slot 208 of the securing device 206 is closed at one end to prevent the leg support 204 from sliding therethrough.

The ankle-foot orthosis 200 includes a fastening device 210 that has elastic properties and extends from the securing device 206 to connect to the leg support 204. The securing device 206 is movable relative to the leg support 204 via the fastening device 210. According to this embodiment, the fastening device 210 is detachably secured to the leg support 204 by a conventional hook and loop fastener system 212. Of course, it will be understood that other fastener systems may be used such as bolts, screws, pins, and snaps. The fastening device 210 enables mobility of the leg support 204 relative to the securing device 206 in the direction D. This feature of the ankle-foot orthosis 200 prevents rubbing between the securing device 206 and a user's body.

The number of layers in the footplate 202 of the ankle-foot orthosis 200 in FIGS. 20 and 21 may be varied, depending on the application and the gait pathology of a user. More specifically, FIGS. 20 and 22 show boundaries between five different layers 220, 222, 224, 226, 228 of the footplate. In this embodiment, a first layer 220 adjacent to the ground surface defines the shape of the footplate, and the subsequent layers 222, 224, 226, 228 superimposed on the first layer 220 have substantially the same shape as the first layer 220 except at a toe portion 229, where they are shortened with each subsequent superimposed layer. The border between each of the superimposed layers 222, 224, 226, 228 is defined as an edge thicknesses generally extending perpendicularly from the adjacent layer.

These thickness differences between adjacent layers create differences in elasticity across the footplate. The result of such layered structure is an ankle-foot orthosis comprising a footplate of different flexibility where certain regions have different stiffness. The layering of the footplate creates different stiffness and flexibility of the footplate, and redistributes forces applied to the foot and where the stiffness gradient of the front part of the footplate corresponds to the ground reaction forces as they are applied by the foot.

FIG. 22 shows different toe and heel heights 232, 234, respectively, of the footplate. By varying the toe height 232 and the heel height 234, one may facilitate roll over of the footplate 202 of the ankle-foot orthosis 200. Since momentum is largest at the heel portion 230 of the footplate 202, it is preferred that the heel portion 230 is the thickest part of the footplate 202. The shape of the heel portion 230 may be determined by the shape of a shoe such that it will fit snugly inside the shoe and but will not excessively rub against the shoe or a user's heel.

The ankle-foot orthosis may be constructed from a variety of materials. According to one embodiment, the ankle-foot orthosis comprises at least two structural layers including a plurality of fibers impregnated with a polymeric material. In this embodiment, the fibers of a first layer adjacent to a ground surface are generally oriented at an oblique angle relative to a line of progression of the footplate extending from a heel portion to a middle portion to a toe portion of the footplate. Preferably, but not limited, the fibers of the first layer extend relative to the line of progression in a range of 15-75°. The polymeric material may be selected from the group consisting of polypropylene, nylon and epoxy resin. The plurality of fibers may be selected from the group consisting of carbon fibers, glass fibers, Kevlar aramid fibers, or other suitable structural fibers.

In embodiments of the ankle-foot orthosis, layers that are superimposed on the first layer may include fibers that are unidirectionally oriented generally parallel to the line of progression of the footplate. Alternatively, the fibers of each structural layer of the footplate may be woven unidirectionally with fibers running substantially parallel to a line of progression of the footplate extending from a heel portion to a middle portion to a toe portion of the footplate.

According to methods for making the leg support of the ankle-foot orthosis and integrating the same with the footplate, such methods are defined in U.S. patent application Ser. No. 10/702,447 (U.S. Published Application 2004/0134500) assigned to the assignee of the present disclosure and incorporated herein by reference.

The embodiments of the ankle-foot orthosis described herein may be provided with silicone padding and a thermoformable tube covering the heel portion of the leg support. This combination results in easier donning of the ankle-foot orthoses and prevents damage of the padding in a vulnerable area. For example, flexible foam padding made from cross-linked, closed cell polyethylene foam may be provided on various parts of the orthosis to add comfort and enhance fit. In the alternative, silicone padding may be used from incompressible silicone that optimizes pressure redistribution. The silicone padding is made of silicone and features a black textile cover. Commercial products include "Ossur AFO Dynamic Foam" and "Ossur Silicone Padding" sold by Ossur hf, of Reykavik, Iceland.

While this embodiment generally shows the leg support as corresponding to a posterior portion of a human leg, the leg support may be modified to extend along at least either the medial or lateral sides of a human leg.

Figure 23:
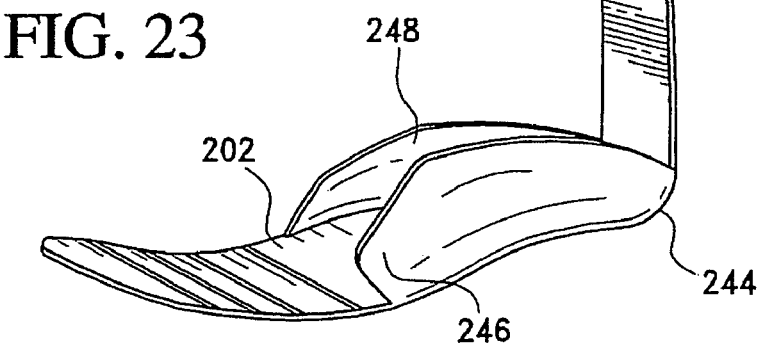
FIG. 23 is a perspective view showing a variation of the ankle-foot orthosis of FIG. 20.

FIG. 23 shows a variation 236 of the embodiment of an ankle-foot orthosis of FIGS. 20-22. According to this embodiment, the ankle-foot orthosis 236 includes at least one calf shell 238 connected to the leg support 204. The calf shell 238 includes at least two curvilinear side portions 240, 242 extending from opposed sides of the leg support 204 and generally extending along a length of a middle and end portions of the leg support 204. A foot shell 244 is connected to the footplate 202 and has at least two curvilinear side portions 246, 248 extending from opposed sides of the footplate 202. The foot shell 244 generally extends along a heel portion and at least a segment of a middle portion of the footplate 202. A suitable connecting element 214 may be used to connect opposed sides of the calf shell 238. This embodiment may be varied to include only the calf shell 238 or the foot shell 240. A user can benefit from the dorsal and plantarflexor assistance that the ankle-foot orthosis provides and further obtain high medial-lateral stability from the calf and foot shells 238, 240. The calf and foot shells 238, 240 can be made of a plastic material or a composite material system, and customized in size for the user.

While in the embodiment shown in FIG. 23 the calf shell 238 is integrated with the leg support 204, the calf shell 238 may be secured to the leg support 204 by any known method that will securely fasten the calf shell 238 to the leg support 204 to provide sufficient stability to a user. Likewise, the foot shell 240 may similarly be integrated with the footplate 202 as shown in FIG. 23 or, in the alternative, the foot shell may be secured to the footplate according to known methods.

Figure 24:
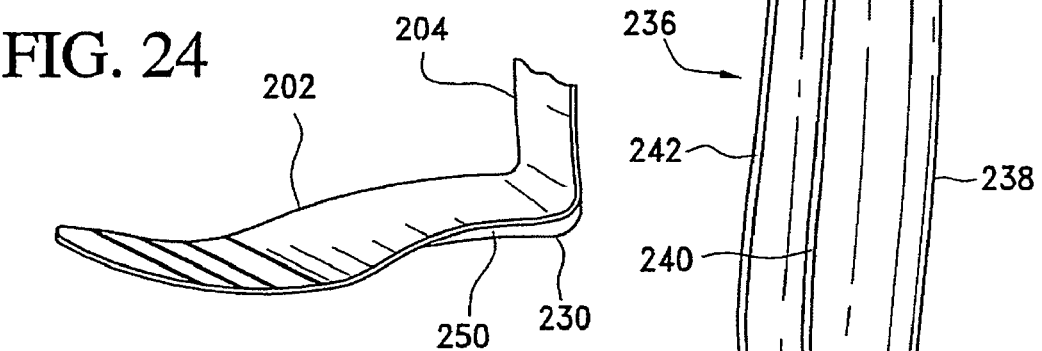
FIG. 24 is a perspective view showing a variation of a footplate of the ankle-foot orthosis of FIG. 20.

FIG. 24 illustrates a variation of the footplate 202 of the ankle-foot orthosis of FIG. 20. According to this variation, the footplate 202 includes a damping device 250 positioned at the heel portion 230 of the footplate 202. The damping device 250 generally extends at an inclined angle relative to the distal surface of the footplate 202.

According to one embodiment, the damping device 250 is a heel wedge that provides smooth heel contact. According to another embodiment, polymers of different stiffness may be used to obtain different stiffness to match an activity level and body weight. In yet another embodiment, the damping device may be separate from the ankle-foot orthosis, but arranged to accommodate the heel portion of the footplate. In this embodiment, the damping device may be a wedge or spring is positionable within the shoe of a user. According to yet another embodiment, the damping device may be a carbon fiber heel plate that extends from the heel portion of the footplate at an inclined angle to provide a spring effect during heel strike.

Figure 25:
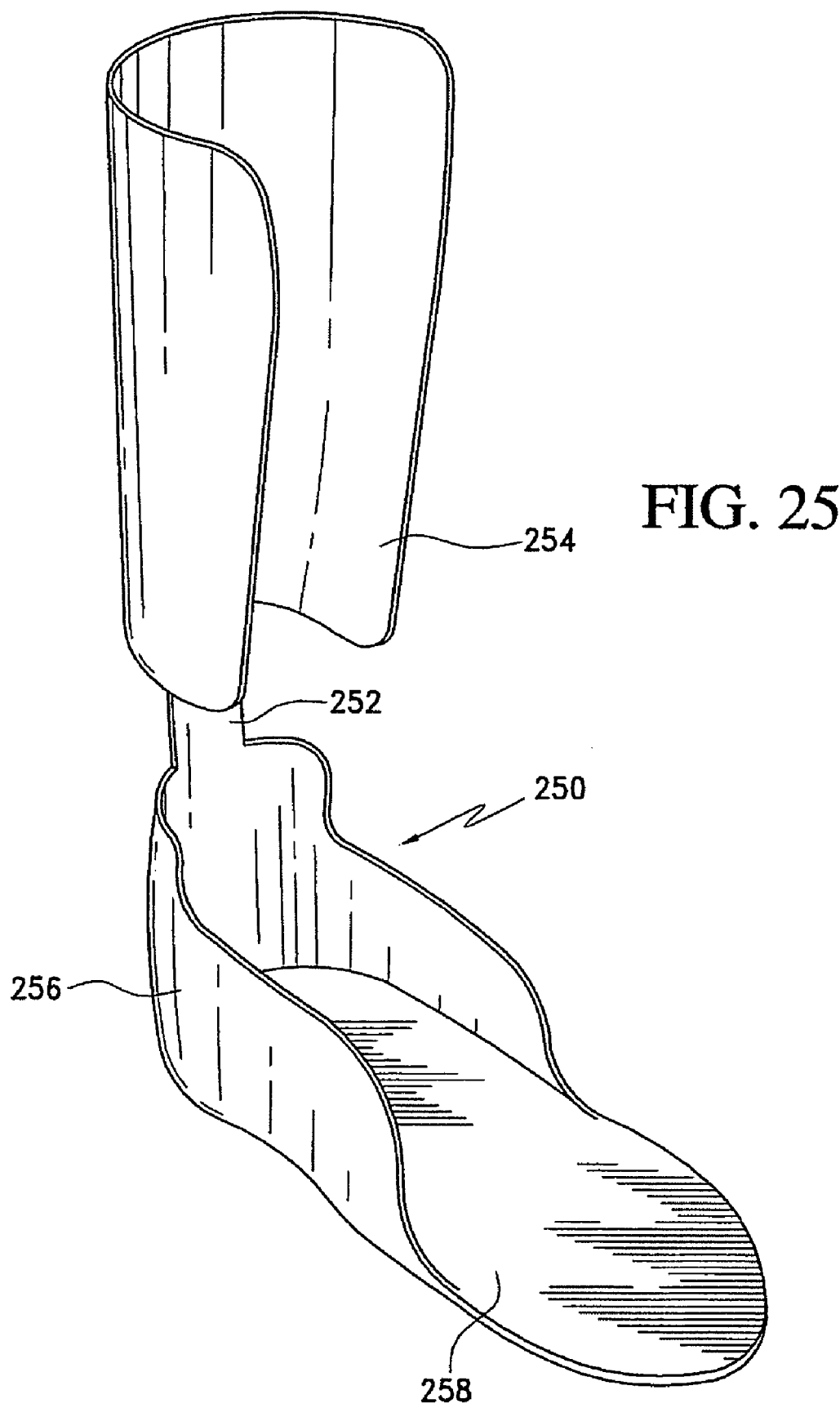
FIG. 25 is a perspective view of an embodiment of an ankle-foot orthosis.

FIG. 25 shows another embodiment of an ankle-foot orthosis 250. According to this embodiment, a spring 252 is integrated with a calf shell 254 and a foot shell 256. The spring 252 and the foot shell 256 are integrated with a footplate 258 of the type described in reference to FIG. 1.

In the ankle-foot orthosis 250, the spring 252, and calf and foot shells 254, 256 may be made from carbon, glass, or Kevlar aramid fibers in combination with an epoxy resin. In the alternative, the spring 252, and calf and foot shells 254, 256 may be constructed from a polymeric material such as polypropylene or polyethylene, and may alternatively be reinforced with bars or other structural elements such as those constructed from metal or composites.

Alternatively, the spring member 252 may be secured to the footplate 258 and the calf and foot shells 254, 256 by known methods described herein for connecting orthotic components together.

Figure 26:
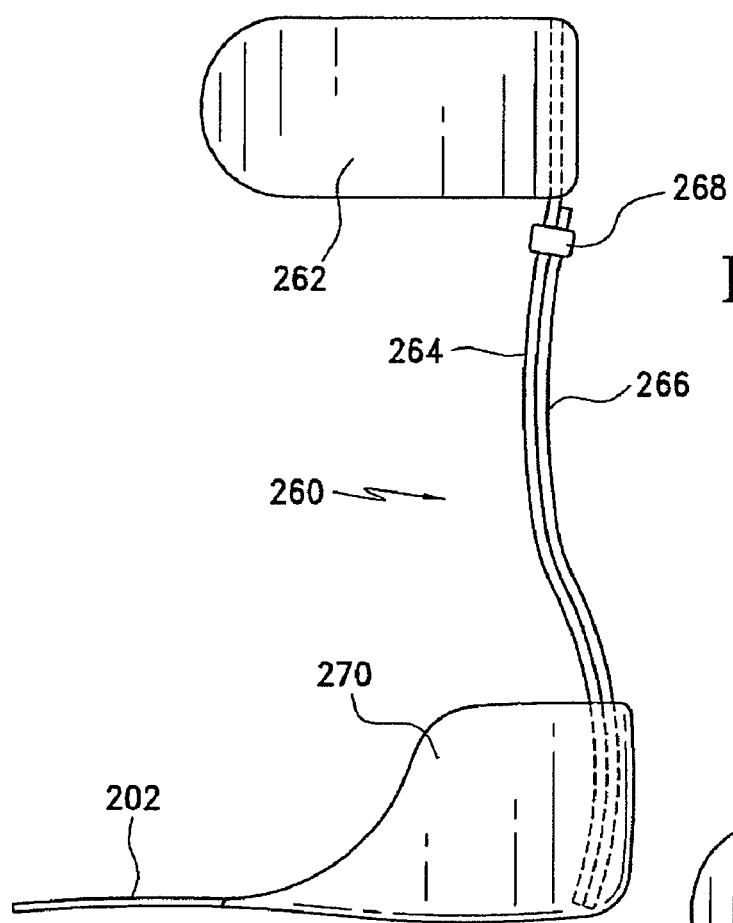
FIGS. 26 and 27 are elevational views showing an embodiment of an ankle-foot orthosis.
Figure 27:
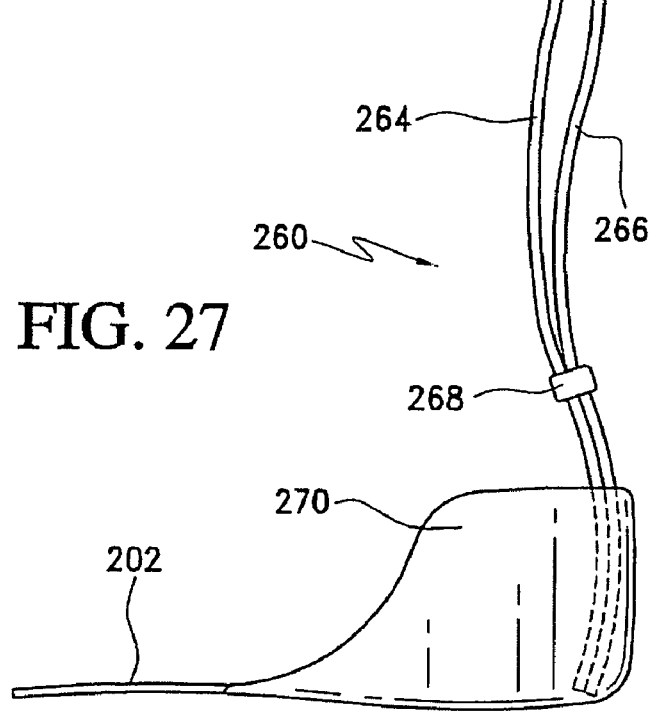

FIGS. 26 and 27 show another embodiment of an ankle-foot orthosis 260 having a first spring member 264 connected to a calf member 262 and a foot member 270. A second spring member 266 is connected with the foot shell 270. The first and second spring members 264, 266 are connected together with a connecting element 268. The connecting element 268 may be a ring, clamp, hook-and-loop type fastener system, or any other connecting element suitable for connecting the first and second spring members 264, 266.

As shown in both FIGS. 26 and 27, the connecting element 268 may be positioned along the length of the first and second spring members 264, 266 to provide for different flexibilities of the ankle-foot orthosis. For example, FIG. 26 shows the connecting element 268 positioned near a proximal portion of the first and second spring members 264, 266. In this configuration, plantarflexion and dorsiflexion of the ankle-foot orthosis 260 are substantially the same. In the alternative, FIG. 27 shows a configuration wherein the ankle-foot orthosis 260 provides greater plantarflexion. Of course, it will be understood that the connecting element 268 may be positioned anywhere between the calf and foot shells 262, 270 along the first and second spring members 264, 266 to obtain desired plantarflexion and dorsiflexion.

The first and second spring members 264, 266 may be integrated with the foot member 270, or secured therewith by methods known to those skilled in the art including adhesives, pins, and a hook and loop fastener system. Moreover, the first spring member 264 may be secured to the calf member 262 using similar methods used to secure to the foot member 270. According to this embodiment, the proximal end of the second spring member 266 is left unattached to the calf member 262 and is free to extend outwardly relative to the first spring member 264 depending on the location of the connecting element 268.

The ankle-foot orthosis 260 includes a footplate 202 generally of the type described above in relation to FIG. 20. The foot member 270 may have a portion that extends around the heel portion of the footplate 202 to reinforce the heel of a user. Furthermore, the calf member 262 may include a fastener element arranged to secure the calf member 262 to a user's leg.

Figure 28:
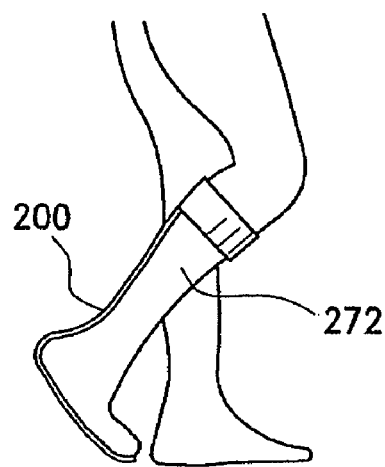
FIGS. 28-30 are schematic views showing dynamic energy storage and energy return of the ankle-foot orthosis of FIG. 20.
Figure 29:
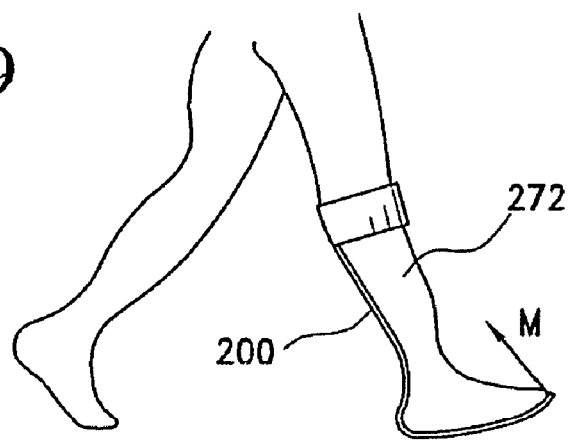
Figure 30:
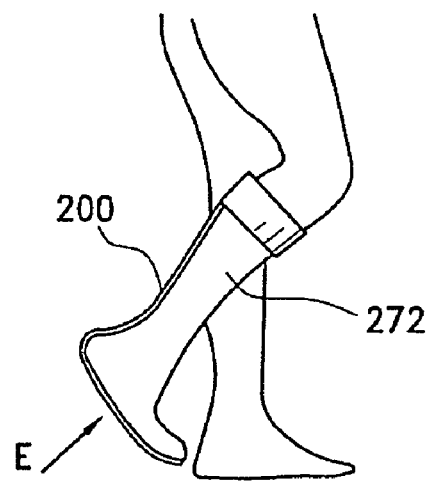

FIGS. 28-30 show dynamic energy storage and energy return of the ankle-foot orthosis 202 of FIG. 20. A person having a normal gait typically requires between 1 and 38 mm of ground clearance in order to avoid dragging their toes over the ground and risk falling. A person lacking the strength to lift up the foot using the dorsiflexors of the ankle risks dragging of the toes over the ground during a mid-swing, which is characterized as the condition called dropfoot. Consequently, individuals with dropfoot have a tendency to change their gait in order to prevent dropfoot from occurring.

Minor support of the ankle and foot 272, as shown in FIG. 28, during this stage of the gait-cycle (100% consisting of 60% stance phase and 40% swing phase) provides sufficient ground clearance and prevents the foot from dragging over the ground. At initial contact, the ankle-foot orthosis 200 provides an additional ankle dorsiflexion moment M (upward motion of the toes and foot marked), of which the user lacks due to insufficient or impaired muscle work of the ankle dorsiflexors (mainly tibialis anterior) of the ankle. The user requires assistance in order to achieve a more normal gait in terms of smooth loading response of the ankle which results in an unforced loading response of the knee. If the heel portion of the footplate is too rigid, the ankle-foot orthosis will act like a lever that will pull the knee forward into forced flexion. Due to the footplate described herein, the flexibility of the footplate will prevent the ankle-foot orthosis to act like a lever.

At the end of stance phase, as shown in FIG. 30, the plantarflexors of the ankle, need to contract in order to create sufficient power to push the foot off the ground and the body forward to ensure progression of the gait. In cases where plantarflexion muscle work is absent or impaired, the spring will compensate or assist that function. Integrating carbon fiber into a spring design allows the spring to benefit from the energetic characteristics of the carbon fibers. Energy is stored when the spring is compressed, in a flexed or bent condition. When the spring decompresses or deflexes, the energy E is released which results in a forward push of the limb which assists the limb to progress into a swing phase, as illustrated in FIG. 30.

Figures 31, 32:
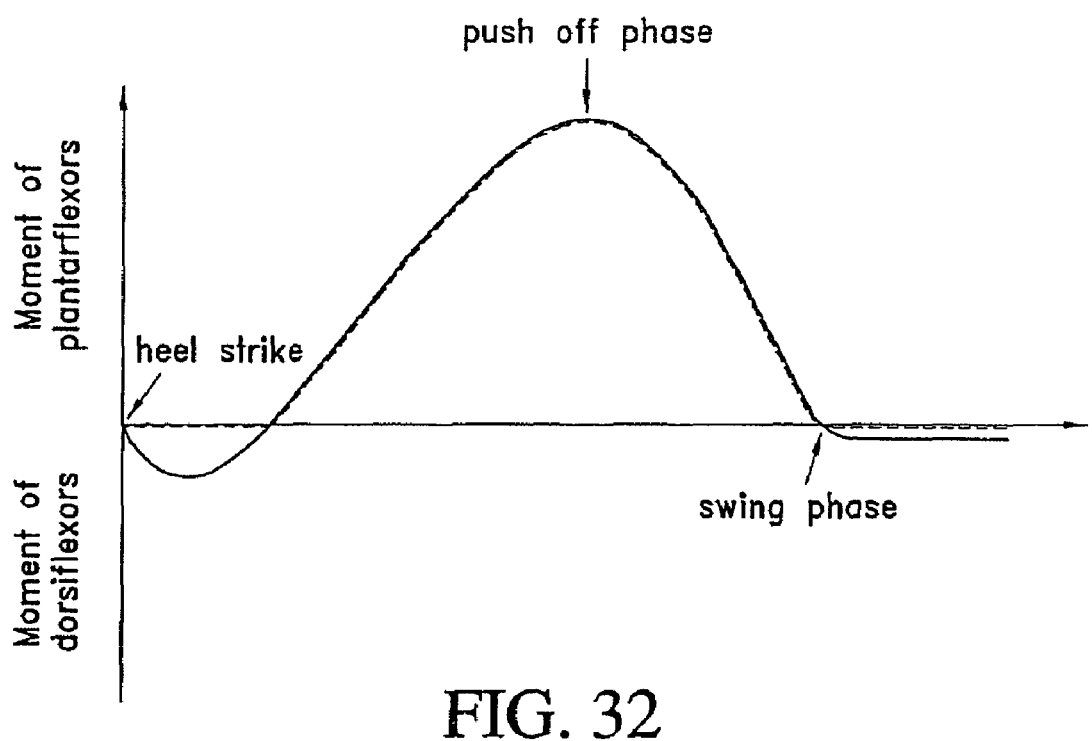
FIG. 31 is a selection chart used in the selection of ankle-foot orthoses.
FIG. 32 is a graphical representation showing momentum of plantarflexors and dorsiflexors during a stance phase and swing phase in one leg.

FIG. 31 represents a selection chart of different ankle foot orthotic device, divided into four categories, foot size, footplate, height of thickest part of the calf, and proximal strap height. The selection chart is further divided into three size categories comprising: small, medium, and large. Thus with the chart shown in FIG. 31, the ankle-foot orthosis may be mass produced.

FIG. 32 shows momentum of plantarflexors and dorsiflexors during a stance phase. The solid line represents the momentum for a healthy foot, while the dotted line shows the momentum for an individual having dropfoot. An objective of the ankle-foot orthosis is to correct gait imperfections so that it follows the path of the solid line. The stiffness of the ankle-foot orthosis should, when dealing with a dropfoot user, aim to solve the crucial momentum difference at the ankle which occurs just after heel strike. If the ankle-foot orthosis has the correct stiffness to provide a normal rate of plantarflexion at heel strike, the ankle-foot orthosis also provides sufficient ground clearance during the swing phase.

The invention claimed is:

1. An ankle-foot orthosis, comprising:
a footplate having a line of progression extending from a heel portion to a middle portion to a toe portion of the footplate, the footplate including at least two superimposed and discrete structural layers each having a different length and extending along at least a segment of a length of the footplate, the footplate defining regions with different thicknesses and stiffness;
a leg support having first and second end portions with a middle portion therebetween, the first end portion connected to the heel portion of the footplate; and
a securing device slidably mounted on the second end portion of the leg support only in a longitudinal direction defined by the second end portion, the securing device including two end portions having a generally curvilinear profile and a connecting element connecting the end portions, the securing device defining a slot having a closed end, side portions and an open end through which the second end portion of the leg support is inserted, the closed end and the side portions delimiting movement of the securing device relative to the leg support only generally in the longitudinal direction.

2. The ankle-foot orthosis according to claim 1, further comprising a fastening device having elastic properties, the fastening device having a first end fixedly secured to the slot of the securing device and a second end fixedly secured to the second end portion of the leg support so at to extend in the direction longitudinal.

3. The ankle-foot orthosis according to claim 1, wherein the leg support includes a spring member connecting to the heel portion of the footplate, and a first member having a center portion connecting to the spring member and two curvilinear side portions extending from the center portion.

4. The ankle-foot orthosis according to claim 3, wherein the spring member and the at least two structural layers of the footplate are formed from a plurality of structural fibers impregnated with a polymeric material, and are integrated together such that the fibers of the footplate are interleaved with the fibers of the spring member.

5. An ankle-foot orthosis, comprising:
a footplate having a line of progression defined from a first end located at a heel portion extending along a middle portion to a second end located at a toe portion of the footplate, the footplate defining regions with different thicknesses and stiffness;
a leg support having first and second end portions with a middle portion therebetween, the first end portion extending from the first end of the footplate and generally extending perpendicular from the line of progression;
a securing device slidably mounted to the leg support in a longitudinal direction defined along the second end portion of the leg support, and the securing device having two end portions generally extending perpendicular to the leg support and a midpoint located between the end portions; and
a generally elastic fastening device defining a first end secured to the midpoint of the securing device and a second end secured to the second end portion of the leg support so at to elastically extend in the longitudinal direction.

6. An ankle-foot orthosis, comprising:
a footplate having a line of progression defined from a first end located at a heel portion extending along a middle portion to a second end located at a toe portion of the footplate, the footplate defining regions with different thicknesses and stiffness;
a continuous and uninterrupted curvilinear leg support having first and second end portions with a middle portion therebetween, the first end portion extending perpendicularly from the heel portion at the line of progression of the footplate;
a securing device slidably mounted at the second end of the leg support, and generally extending perpendicular relative to the leg support, the securing device defining a slot having a closed end and an open end through which the second end portion of the leg support is inserted, the closed end delimiting movement of the securing device relative to the leg support; and a fastening device secured to both the second end portion of the leg support and the slot of the securing device, and delimiting movement of the securing device relative to the leg support along a generally longitudinal segment of the second end portion.

7. The ankle-foot orthosis according to claim 6, wherein the fastening device has elastic properties generally in a longitudinal direction of the second end portion of the leg support.

* * * * *